United States Patent [19]

Mazurek

[11] Patent Number: 5,026,947
[45] Date of Patent: Jun. 25, 1991

[54] METHANE CONVERSION PROCESS
[75] Inventor: Harry Mazurek, Bala Cynwyd, Pa.
[73] Assignee: Atlantic Richfield Company, Los Angeles, Calif.
[21] Appl. No.: 506,129
[22] Filed: Apr. 9, 1990
[51] Int. Cl.⁵ .............................................. C07C 2/00
[52] U.S. Cl. .................................... 585/500; 585/900
[58] Field of Search ............... 585/500, 415, 417, 541, 585/654, 658, 661, 943, 700

[56] References Cited

U.S. PATENT DOCUMENTS

| 4,443,646 | 4/1984 | Jones et al. | 585/500 |
| 4,443,649 | 4/1984 | Jones et al. | 585/500 |
| 4,444,984 | 4/1984 | Jones et al. | 585/500 |
| 4,523,050 | 6/1985 | Jones et al. | 585/500 |
| 4,727,211 | 2/1988 | Gaffney | 585/943 |
| 4,727,212 | 2/1988 | Gaffney | 585/943 |
| 4,788,372 | 11/1988 | Gaffney | 585/943 |
| 4,879,427 | 11/1989 | Sofranko | 585/943 |
| 4,935,572 | 6/1990 | Erekson et al. | 585/943 |

Primary Examiner—Curtis R. Davis
Attorney, Agent, or Firm—William C. Long

[57] ABSTRACT

A process for the oxidative conversion of methane to higher hydrocarbons is provided wherein a mixture of methane and gaseous oxidant is contacting at reactive conditions with a reducible metal oxide containing solid contact agent, the improvement comprising periodically discontinuing methane feed to the solid contact agent so that the solid agent is maintained in a more active and highly oxidized state.

3 Claims, No Drawings

METHANE CONVERSION PROCESS

BACKGROUND OF THE INVENTION

1. Field of the Invention

The present invention relates to the oxidative conversion of methane to higher hydrocarbons. In particular, the invention relates to a process whereby a mixed feed comprised of methane and molecular oxygen is contacted with a contact solid containing a reducible metal oxide at reacted conditions effective to form higher hydrocarbons and water wherein the reducible metal oxide is periodically contacted with molecular oxygen in the absence of methane at conditions effective to substantially fully oxidize the reducible metal oxide. By this process, the reducible metal oxide is maintained in a more active state during methane conversion.

2. Description of the Prior Art

This invention relates to the conversion of methane to higher hydrocarbons. A particular application of this invention is a method for converting natural gas to more readily transportable material.

Methane can be converted to higher hydrocarbons by reaction at conditions of elevated temperature—e.g., a temperature selected within the range from about 500° C. to about 1000° C. For example, methane can be contacted with an oxidative synthesizing agent containing a reducible metal oxide in the absence of gaseous oxidant at such elevated temperatures in order to produce higher hydrocarbons in a cyclic "redox" mode, the metal oxide being periodically reoxidized as with molecular oxygen. Reducible oxides of several metals have been identified which are capable of converting methane to higher hydrocarbons. In particular, oxides of manganese, tin, indium, germanium, lead antimony, bismuth, praseodymium, terbium, cerium, iron and ruthernium are most useful. See commonly-assigned U.S. Pat. Nos. 4,443,644 (Sb); 4,443,649 (Mn); 4,444,984 (Sn); 4,445,648 (In); 4,443,645 (Ge); 4,443,674 (Pb); 4,443,646 (Bi); 4,499,323 (Pr); 4,499,324 (Ce); and 4,593,139 (Ru). See also commonly-assigned U.S. Pat. No. 4,721,828.

Commonly-assigned U.S. Pat. No. 4,554,395 discloses and claims a process which comprises contacting methane with an oxidative synthesizing agent under elevated pressure (2-100 atmospheres) to produce greater amounts of $C_2+$ hydrocarbon products.

Commonly-assigned U.S. Pat. No. 4,560,821 discloses and claims a process for the conversion of methane to higher hydrocarbons which comprises contacting methane with particles comprising an oxidative synthesizing agent which particles recirculate between two physically separate zones—a methane contact zone and an oxygen contact zone.

U.S. Pat. No. 4,499,322 discloses and claims a process for the conversion of methane to higher hydrocarbon and comprises contacting methane with an oxidative synthesizing agent containing a promoting amount of alkali metal and/or compounds thereof.

U.S. Pat. No. 4,495,374 discloses and claims a process for the conversion of methane to higher hydrocarbons which comprises contacting methane with an oxidative synthesizing agent containing a promoting amount of alkaline earth metal and/or compounds thereof.

Hinsen and Baerns report studies of a continuous "cofeed" mode for the oxidative coupling of methane wherein regeneration air is cofed with methane feed. Hinsen, W. and Baerns, M., "Oxidative Koppling von Methan zu $C_2$—Kohlenwasserstoffen in Gegenwart unterschiedlicher Katalsatoren", Chemiker-Zeitung, Vol. 107, No. 718, pp. 223–226 (1983). Using a catalyst based on lead oxide and gamma-alumina in a fixed bed reactor operated at 1 atmosphere total pressure and 600–750 degrees C., they report results of approximately 53% selectivity to ethane and ethylene at 8% methane conversion for a feed consisting of about 50% methane, 25% air and 25% nitrogen. Other metal oxides studied by Hinsen and Baerns included oxides of Bi, Sb, Sn and Mn.

U.S. Pat. No. 4,523,049 discloses and claims a process for converting methane to higher hydrocarbons in a cofeed mode which comprises contacting methane and an oxygen-containing gas with a solid comprising a reducible metal oxide and an alkali/alkaline earth metal promoter.

U.S. Pat. No. 4,523,050 discloses and claims a process for converting methane to higher hydrocarbons in a cofeed mode which comprises contacting methane and an oxygen-containing gas with a manganese silicate.

Commonly-assigned copending U.S. Pat. No. 4,788,372 discloses and claims a method for converting methane to higher hydrocarbons wherein methane and added water are contacted in the substantial absence of added gaseous oxidant with a solid comprising at least one reducible metal oxide.

Commonly-assigned U.S. Pat. No. 4,801,762 discloses and claims a method for converting methane to higher hydrocarbons wherein methane and a gaseous oxidant together with added water are contacted with a nonacidic solid and/or a reducible metal oxide.

Other relevant patents include U.S. Pat. Nos. 4,777,312, 4,795,849 and the like.

The reaction products of the foregoing processes are hydrocarbons, carbon oxides, coke and water.

The methane conversion reaction can be carried out by contacting methane with the reducible metal oxide in the fluidized bed reaction systems as well as in fixed bed systems.

SUMMARY OF THE INVENTION

It has now been found that in oxidative conversions of methane carried out in the "cofeed" mode and using a contact solid comprised of a reducible metal oxide, the oxidation state of the metal oxide during methane conversion is partially reduced even though the metal oxide is continuously contacted at reactive conditions with the feed gas comprised of methane and molecular oxygen. In the partially reduced state, the metal oxide is less active in effecting oxygen transfer and methane conversion. In accordance with this invention, methane and oxygen are contacted with reducible metal oxide in the "cofeed" mode to convert methane to higher hydrocarbons and co-product water, and the metal oxide is periodically reacted with oxygen in the absence of methane whereby the oxide is substantially completely oxidized. As a result, the metal oxide is on the average more active and effective for carrying out the oxidative conversion of the methane feed.

DETAILED DESCRIPTION OF THE INVENTION

The present invention is applicable to processes of the "cofeed" type where a mixture of oxygen and methane is contacted with a reducible metal oxide to form higher hydrocarbons and water. The reducible metal oxides and promoters set forth, for example, in U.S. Pat. Nos.

4,523,049, 4,801,762, 4,523,050, 4,634,800, 4,670,619 as well as the reaction conditions set forth therein can be used in this invention.

With regard to reducible metal oxides, while such solids are sometimes referred to as "catalysts" it will be understood that, under conditions of use, non-acidic solids comprising a reducible metal oxide act as selective oxidants, and, therefore, take on the characteristics of a reactant during use. Thus, for example, the term "Mn-containing oxides" is meant to embrace both reducible oxides of Mn and reduced oxides of Mn, it being understood reducible oxides comprise the principal active component of the compositions.

In their active state, such catalysts comprise at least one reducible oxide of at least one metal, which oxide when contacted with methane at synthesizing conditions (e.g., at a temperature within the range of about 500° to 1000° C.) produces higher hydrocarbon products, coproduct water and a reduced metal oxide. The term "reducible" is used to identify those oxides of metals which are reduced under the aforesaid conditions. The term "reducible oxides of metals" includes: (1) compounds described by the general formula $M_xO_y$ wherein M is a metal and x and y designate the relative atomic proportions of metal and oxygen in the composition and/or (2) one or more oxygen-containing metal compounds (i.e., compounds containing elements in addition to the metal and O), provided that such oxides and compounds have the capability of producing higher hydrocarbon products from methane as described herein.

Effective agents for the conversion of methane to higher hydrocarbons have previously been found to comprise reducible oxides of metals selected from the group consisting of manganese, tin, indium, germanium, antimony, lead, bismuth and mixtures thereof. See U.S. Pat. Nos. 4,443,649; 4,444,984; 4,443,648, 4,443,645; 4,443,647; 4,443,644; and 4,443,646. Reducible oxides of manganese are particularly preferred catalyst components.

Reducible oxides of cerium, praseodymium and terbium have also been found to be effective for the conversion of methane to higher hydrocarbons, particularly associated with an alkali metal component and/or an alkaline earth metal component. See U.S. Pat. Nos. 4,499,324 (Ce) and 4,499,323 (Pr) and also see commonly-assigned U.S. patent application Ser. No. 06/600,918 (Tb) now abandoned.

Reducible oxides of iron and ruthenium are also effective, particularly when associated with an alkali or alkaline earth component. See commonly-assigned U.S. patent application Ser. No. 06/600,730 (Fe) now abandoned and U.S. Pat. Nos. 4,489,215 and 4,593,139 (Ru).

Alkali and alkaline earth metals and compounds thereof have been found to improve the hydrocarbon product selectivity of reducible metal oxides. The further incorporation of phosphorous into solids promoted by alkali or alkaline earth components enhances catalyst stability. See commonly-assigned U.S. Pat. Nos. 4,499,322 and 4,495,374, the entire content of which are incorporated herein by reference. Alkali metals are selected from the group consisting of lithium, sodium, potassium, rubidium and cesium. Lithium, sodium and potassium, and especially lithium and sodium, are preferred alkali metals. Alkaline earth metals are selected from the group consisting of magnesium, calcium, strontium and barium. Presently preferred members of this group are magnesium and calcium. Compositions derived from magnesia have been found to be particularly effective catalysts materials. Boron and compounds thereof are also desirably present in the reducible metal oxide catalyst employed in the process of this invention. See commonly-assigned copending U.S. patent application Ser. No. 06/877,574, the entire content of which is incorporated herein by reference. One class of boron-promoted compositions useful in the process of this invention comprises:

(1) at least one reducible metal oxide,
(2) at least one member of the group consisting of boron and compounds thereof, and
(3) at least one member of the group consisting of oxides of alkaline earth metals.

A related class of catalyst compositions further comprises at least one alkali metal or compound thereof. Sodium and lithium are preferred alkali metal components.

One further, special class of catalysts compositions useful in the process of this invention are mixed oxides of sodium, magnesium, manganese and boron characterized by the presence of the crystalline compound $NaB_2Mg_4Mn_2O_x$ wherein x is the number of oxygen atoms required by the valence states of the other elements, said compound having a distinguishing x-ray diffraction pattern. In its most active form, the compound is believed to correspond to the formula $NaB_2Mg_4Mn_2O_{11}$. While this crystalline compound has been found to be associated with highly effective oxidant compositions, it has further been found that still better results are obtained when the oxidant is characterized by both: (1) the presence of crystalline compound $NaB_2Mg_4Mn_2O_x$ and (2) a stoichiometric excess of Mn relative to at least one of the other elements of the crystalline compound. In currently preferred oxidants of this type, a stoichiometric excess of Mn relative to B is provided. In a still more specific preferred embodiment, excess amounts of Na and Mg as well as Mn are present in the mixed oxide composition relative to the amounts required by the amount of boron present to satisfy the stoichiometry of the compound $NaB_2Mg_4Mn_2O_x$.

Further examples of components which may be present in the catalysts used in the process of this invention are halogen and chalcogen components. Such components may be added either during preparation of the catalysts or during use. Methane conversion processes employing halogen-promoted reducible metal oxides are disclosed in U.S. Pat. No. 4,544,784. Methane conversion processes employing halcogen-promoted, reducible metal oxides are disclosed in U.S. Pat. No. 4,544,785.

The reducible metal oxides compositions may be supported by or diluted with support materials such as silica, alumina, titania, zirconia and the like, and combinations thereof. When supports are employed, alkaline earth oxides, especially magnesia, are preferred.

The catalysts are conveniently prepared by any of the methods associated with similar compositions known in the art. Thus, such methods as precipitation, co-precipitation, impregnating, granulation, spray drying or dry-mixing can be used. Supported solids may be prepared by methods such as absorption, impregnation, precipitation, co-precipitation and dry-mixing. For example, compounds of Mn,Sn,In,Ge,Pb,Sb,Bi,Pr,Tb,Ce,Fe and/or Ru may be combined with compounds of other components in any suitable way. Substantially any compound of the components can be employed. Compounds typically used would be oxides or organic or inorganic salts of the recited components.

To illustrate, when preparing a catalyst containing: (1) a reducible metal oxide component (e.g., Mn), (2) an alkali metal component, (3) a boron component and (4) an alkaline earth component; one suitable method of preparation is to impregnate compounds of the fourth component of the composition with solutions of compounds of Mn, alkali metals and/or boron. Suitable compounds for impregnation include the acetates, acetyl acetonates, oxides, carbides, carbonates, hydroxides, formates, oxalates, nitrates, phosphates, sulfates, sulfides, tartrates, fluorides, chlorides, bromides or iodides. After impregnation, the preparation is dried to remove solvent and the dried solid is calcined at a temperature selected within the range of about 300° to 1200° C. Particular calcination temperatures will vary depending on the compounds employed. Preferably, the alkaline earth component is provided as the oxide. Preferably, the alkali metal component is provided as a basic composition of the alkali metal(s). Examples are sodium hydroxide, sodium acetate, lithium hydroxide, lithium acetate, etc. When P is employed as an additive, it has been found desirable to add the alkali metal and P to the composition as compounds such as the orthophosphates, metaphosphates and pyrophosphates of alkali metals. Pyrophosphates are preferred. Sodium pyrophosphate is particularly preferred. Preferably, the boron component is provided as boric acid, boric oxide (or anhydride), alkali metal borates, boranes, borohydrides, etc., especially boric acid or oxide.

Formation of the crystalline compound $NaB_2Mg_4Mn_2O_x$ may be accomplished by reacting active compounds of the substituent elements. A suitable mixture of the reactive compounds is formed and heated for a time sufficient to form the crystalline material. Typically, a temperature of about 850° to about 950° C. is sufficient. When preparing mixed oxide compositions characterized by the presence of other crystalline compounds, the composition is desirably incorporated with binders or matrix materials such as silica, alumina, titania, zirconia, magnesia and the like.

Regardless of which particular catalyst is prepared or how the components are combined, the resulting composite will generally be dried and may or may not be calcined at elevated temperatures prior to the reducing agent treatment of the present invention.

Preferably, methane is contacted with reducible metal oxides in the substantial absence of catalytically effective nickel, noble metals and compounds thereof, (i.e., nickel, rhodium, palladium, silver, osmium, iridium, platinum and gold) to minimize the deleterious catalytic effects thereof. These metals, when contacted with methane at the temperatures employed in the methane contacting step of the present invention, tend to promote coke formation, and the metal oxides tend to promote the formation of combustion products rather than the desired hydrocarbons. The term "catalytically effective" is used herein to identify the quantity of one or more of nickel and the nobble metals and compounds thereof which substantially changes the distribution of products obtained in the method of this invention relative to such contacting in the absence of such metals and compounds thereof.

In carrying out the methane conversion reaction, operating temperatures are generally within the range of about 300° to about 1200° C.

The temperature selected may depend in part on the particular reducible metal oxide(s) employed. Best results for contact solids containing manganese have been found at operating temperatures within the range of about 800° to 900° C.

The methane-containing hydrocarbon feedstock employed in the process of this invention may contain in addition to methane other hydrocarbon or non-hydrocarbon components. The methane content of the hydrocarbon portion of the feedstock, however, will typically be within the range of about 40 to 100 vol. %, preferably within the range of about 80 to 100 vol. %, more preferably within the range of about 90 to 100 vol. %.

Essential to aspect of the present invention is the provision of molecular oxygen as part of the feed to the oxidative conversion step. The oxygen-containing gas generally comprises molecular oxygen: other gases such as nitrogen and carbon oxides may be present. A preferred oxygen-containing gas is air.

The ratio of hydrocarbon feedstock to oxygen-containing gas is not narrowly critical to the present invention. Generally, it is desirable to control the hydrocarbon/oxygen molar ratio to avoid the formation of gaseous mixtures within the flammable region. It is preferred to maintain the volume ratio of hydrocarbon/oxygen within the range of about 0.1-100:1, more preferably within the range of about 1-50:1. Methane/air feed mixtures containing about 50 to 90 volume % methane have been found to comprise a desirable feedstream. Further dilution of the feedstream with gases such as nitrogen are not necessary.

The provision of added water during at least a portion of the oxidative conversion is advantageous as described in U.S. Pat. No. 4,801,762. Preferably, the mole ratio of added water to methane in the gas to be contacted is less than about 10. More preferably, this mole ratio is in the range of about 0.01 to about 6, still more preferably about 0.05 to about 4.0. The added water may be combined with the methane-containing gas and/or the oxygen-containing gas prior to contacting the non-acidic solid. For example, the methane-containing gas or the oxygen-containing gas may be contacted with water so that the gas "picks up" a predetermined, controlled amount of added water prior to the methane/solid contacting. Alternatively, a predetermined, controlled amount of water, e.g., steam, can be injected into the methane-containing gas and/or the oxygen-containing gas and/or directly into the contact zone or zones.

Operating pressures are not critical to the presently claimed invention. However, both general system pressure and partial pressures of methane and water have been found to affect overall results. Preferred general system pressures are within the range of about 0.1 to 30 atmospheres.

The space velocity of the gaseous reaction streams are similarly not critical to the presently claimed invention, but have been found to affect overall results. Preferred total gas hourly space velocities are within the range of about 100 to 300,000 hr.$^{-1}$, more preferably within the range of about 600 to 100,000 hr.$^{-1}$.

A critical aspect of the present invention is the periodic re-oxidation of the reducible metal oxide containing contact solid. This is accomplished by discontinuing the feeding of methane to the solid contact zone with the result that the contact solid at substantially the methane conversion conditions is contacted with molecular oxygen in the absence of methane at reactive conditions effective to substantially completely oxidize the reducible metal oxide. During this reoxidation, care must be exercised to avoid an excessive exotherm which might damage the contact solid. Generally, the flow of oxygen during the reoxidation is regulated to avoid an exotherm above about 900° C. Upon completion of the reoxidation, flow of methane to the contact solid is resumed and the methane oxidative in the cofeed mode continued.

Generally, within practical limits the reoxidation of the reducible metal oxide containing contact solid is done as frequently as possible in order that the average oxidation state of the contact solid be as high as possible in order to achieve the best methane conversion results. Reoxidation every 5 seconds to 2 minutes is a good range, each reoxidation lasting until the catalyst temperature is lowered to reaction temperature.

The solids may be maintained in the contact zone as fixed, moving or fluidized beds of solids. A fixed bed of contact solids is currently preferred for the method of this invention.

The effluent from the contact zones contains higher hydrocarbon products (e.g., ethylene, ethane and other light hydrocarbons), carbon oxides, water and unreacted hydrocarbons (e.g., methane). Higher hydrocarbons may be recovered from the effluent and, if desired, subjected to further processing using techniques known to those skilled in the art. Unreacted methane may be recovered and recycled to the contact zone.

The following examples illustrate the invention:

EXAMPLE 1

Methane was oxidatively converted to higher hydrocarbons by contacting a feed mixture of equal volumes of steam, methane and air with a solid reducible metal oxide contact agent consisting of mixed oxides of lithium, boron, manganese and magnesium. The atomic ratio of Li: B: Mn: Mg was 0.5: 0.5: 1: 2.75. The feed also contained 10 ppm $H_2S$ based in methane.

The contact agent was preheated to 850° C. and a mixture of equal volumes of steam, air and methane (Run 1) was contacted with the contact agent. Methane weight hourly space velocity was 3.34 hr.$^{-1}$.

After 20 seconds reaction time, during which reaction temperature increased to about 870° C. due to the reaction exotherm, the supply of methane was cut off with the air and steam flow continuing to the contact agent. When the contact agent temperature had declined to the original 850° C., methane flow was re-established and the cycle repeated.

The following table shows the results obtained:

TABLE 1

| | $CH_4$ Conversion, % | Selectivity to $C_2^+$ Hydrocarbons, % | Yield of $C_2^+$ Hydrocarbons, % |
|---|---|---|---|
| Run 1 | 43.0 | 66.0 | 28.5 |

COMPARATIVE EXAMPLES

By way of contrast, runs over a contact agent having the same composition as in Run 1 were carried out at 850° C. in the conventional "cofeed" and "redox" mode. In the case of the cofeed runs, methane liquid hourly space velocity was 3.6, equal volumes of methane and air (Run 2) and methane, air and water vapor (Run 3) were fed. In the case of the redox runs, methane at a weight hourly space velocity of 3.3 (Run 4) was passed over the oxidized contact material for 15 seconds. Methane flow was cut off, the contact agent purged with nitrogen and reoxidized by contact with air, usually for 30 minutes. Air flow was discontinued and the contact agent again purged with nitrogen before methane was again fed and the cycle repeated. In Run 5 water vapor was fed with the methane in a volume ratio of water vapor to methane of 0.25:1.

The following table shows the results obtained:

TABLE 2

| | $CH_4$ Conversion, % | Selectivity to $C_2^+$ Hydrocarbons, % | Yield of $C_2^+$ Hydrocarbons, % |
|---|---|---|---|
| Run 2 | 25.0 | 71.0 | 17.8 |
| Run 3 | 26.0 | 77.0 | 20.0 |
| Run 4 | 16.0 | 91.0 | 14.6 |
| Run 5 | 22.0 | 93.0 | 20.5 |

The results presented above clearly demonstrate the improved results which are achieved through practice of the invention compared to those achieved in accordance with prior practices.

I claim:

1. In a process for the oxidative conversion of methane to higher hydrocarbons wherein a feed comprised of a mixture of methane and oxygen is contacted with a reducible metal oxide at reactive conditions effective to form higher hydrocarbons and water, the improvement which comprises maintaining the said reducible metal oxide in a high oxidation state in the process by periodically discontinuing methane feed while maintaining molecular oxygen feed and contacting said reducible metal oxide with said molecular oxygen in the absence of said methane at conditions effective to substantially fully oxidize said reducible metal oxide.

2. The method of claim 1 wherein the temperature of the reducible metal oxide is maintained at 900° C. or lower during oxidation in the absence of methane.

3. The method of claim 1 wherein steam is added to the feed.

* * * * *